US008810795B2

(12) United States Patent
Chen

(10) Patent No.: US 8,810,795 B2
(45) Date of Patent: Aug. 19, 2014

(54) OPTICAL DETECTION SYSTEM

(71) Applicant: National Yang-Ming University, Taipei (TW)

(72) Inventor: How-Foo Chen, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 13/682,174

(22) Filed: Nov. 20, 2012

(65) Prior Publication Data

US 2013/0342839 A1    Dec. 26, 2013

(30) Foreign Application Priority Data

Jun. 25, 2012   (TW) .............................. 101122701 A

(51) Int. Cl.
    *G01N 21/55*    (2014.01)
    *G01J 4/04*     (2006.01)
(52) U.S. Cl.
    CPC .......................................... *G01J 4/04* (2013.01)
    USPC .......................................... 356/445; 356/244

(58) Field of Classification Search
    USPC ......... 356/445, 369, 602, 607–608, 614, 622;
                                          250/201.1, 216, 221, 276
    See application file for complete search history.

(56) References Cited

U.S. PATENT DOCUMENTS

2009/0174883 A1*   7/2009   Zawaideh et al. ............. 356/369
2012/0170049 A1*   7/2012   Doran ........................... 356/496

* cited by examiner

*Primary Examiner* — Tri T Ton
(74) *Attorney, Agent, or Firm* — Muncy, Geissler, Olds & Lowe, P.C.

(57) ABSTRACT

The present invention provides an optical detection system in which a first mirror of the control unit is used to receive light beam and redirect it into a first one-dimensional off-axis parabolic mirror. The first one-dimensional off-axis parabolic mirror then directs the light beam to a cylindrical lens. Through the mechanism of reflection, the cylindrical lens further directs the light beam to a second one-dimensional off-axis parabolic mirror. The second one-dimensional off-axis parabolic mirror then directs the light beam into a second mirror. The detection unit of the system is used to detect the light beam coming from the control unit, so as to convert the light signals into electric signals for the analysis in the process unit afterwards.

18 Claims, 4 Drawing Sheets

OPTICAL DETECTION SYSTEM

CROSS-REFERENCE TO RELATED APPLICATIONS

This Non-provisional application claims priority under 35 U.S.C. §119(a) on Patent Application No(s). 101122701 filed in Taiwan, Republic of China Jun. 25, 2012, the entire contents of which are hereby incorporated by reference.

FIELD OF THE INVENTION

This invention relates to an optical detection system, particularly an optical detection system that can utilize Surface Plasmon Waves and Localized Surface Plasmon Waves.

BACKGROUND OF THE INVENTION

With optical detection system, an object can be detected to gain detailed analysis information, in which the application of surface plasmon waves is to implement analysis of the object through the Surface Plasmon Waves activated by light. Currently, the application is widely applied to biological detection and its molecular dynamics research including biosensor, immunodiagnosis and dynamic analysis of antibody and antigen. Through the chemical binding specificity of the antigen and its corresponding antibody, surface plasmon resonance is mainly applied to the dynamic analysis of the chemical binding between antibody and antigen in the research of biomedical science. The derivative applications include the detection of the existence of biomolecule, detection of subspecies of certain pathogenic bacteria, and detection and categorization of certain virus, among which the detection of the existence of biomolecule is currently the major derivative application of surface plasmon waves in biomedical science, such as inflammatory biomarker, the detection of cardiovascular disease using C-reactive protein, the detection of subspecies of certain pathogenic bacteria, and detection and categorization of certain virus.

The basic framework of a surface plasmon wave sensor is a sensing device that detects a change of the resonance condition between an incident light beam and surface plasmon wave on the interface of metal and dielectrics, and the change of the resonance is caused by the refractive index change of the dielectrics, which can be a result of antigen capture or molecular binding, molecular folding, deformation, or any other changes of the tested material close to or on the interface.

The change can be gained from measuring the optical property of the reflected light beam. Regarding the measurement on different optical properties of the reflected light beam, the measuring modes can be classified as angle, amplitude, wavelength, and phase modes. As for the operation procedure, though the measuring modes of amplitude and phase are static, the light path of the incident light beam needs to be adjusted before implementing measurement to receive the maximum sensitivity: the incident angle of the laser beam to obtain the largest change in amplitude with the refractive index change of dielectric substance, or the resonance angle for phase mode has to be located. When the system design does not allow incident angle adjustment, the detectable range of refractive index and sensitivity will be much restricted. Only when the system is operated under wavelength mode, a satisfied measuring dynamic range can be gained without changing the incident angle, except that the sensitivity is not as good as phase mode measurement. Moreover, the angle measuring mode is inherently dynamic, the incident angle of the light beam needs to be scanned repetitively during the measurement.

Traditional surface plasmon resonance instruments implementing corresponding rotation using two-arm rotating stage, in order to achieve the capability of adjusting the incident angle of the light beam. However, there are several disadvantages:

a. The incident light source and the receiving terminal are not fixed, which will limit the size, weight, and complexity of the light source system and the optical detection system. This also means that a detection method of a phase mode and an amplitude mode will be restricted.

b. The resolution, accuracy, and stability, of a rotation stage are not as good as a linear motorized stage. Besides, two rotation stages are not cost effective compared to a linear stage.

c. Due to the structural limitation of optical elements, the coupling side of the coupling prism is mainly oriented vertically. When matching oil is used to couple a glass slide and the prism, the matching oil is easy to evaporate after a long time use. As a result, the system stability and measurement consistency in the long time use are not easy to maintain.

d. The vertical orientation of the prism coupling face is not suitable for the design and operation of a microfluidics chip.

e. The vertical orientation of prism coupling face cannot be incorporated into an image system, particularly a microscopy system, because the design of vertical light path for image capture is mainly adopted in a microscopy system.

There is another way to adjust the incident angle of the light beam by incorporating a galvo mirror scanning system. In this method, the light path of the reflected beam will be deflected from the designed incidence angle of the optical elements and detectors in the detection system. This beam deflection caused by incident angle tuning will result in the impossibility of implementing phase detection. However, phase detection usually has higher sensitivity.

In the last few years, although the models of all kinds of detection modes have different advantages, there is still a lack of the design that can integrate several modes into one device. With current devices, operation modes (resonance angle mode and amplitude measuring mode) with a large dynamic range usually cannot meet the requirement of high sensitivity, and the incident angle of the light beam in a device performing a phase mode is usually fixed; therefore, its dynamic range is extremely small.

U.S. Pat. No. 7,265,844 discloses a horizontal surface plasmon resonance instrument that is claimed to be able to adjust the incidence angle through a complicated mechanical motion and track with special curves, and thus fix the position of the light source and the optical detection unit. However, the accuracy and stability are not satisfying.

Moreover, FIG. 1 is also a prior art, which is the illustration of surface Plasmon wave detection system disclosed by the inventor of the present invention. As illustrated, the surface Plasmon system 100 includes a light source unit 110, a control unit 120, a detection unit 130 and a process unit 140.

The light source unit 110 includes: a semiconductor laser 111, a polarizing beam splitter 112 and a half-wave plate 113, used to direct the light into the control unit 120.

The control unit 120 includes: a motorized stage 121, a right angled triangle mirror 122, two-dimensional parabolic mirror 123a and 123b and a hemispherical lens 124. The light is directed by the triangle mirror 122 into the two-dimensional parabolic mirror 123a. The two-dimensional parabolic mirror 123a first directs the light into the hemisphere lens 124, and the hemisphere lens 124 then directs the light into the two-dimensional parabolic mirror 123b. At last, the light is directed into the triangle mirror 122 through the two-dimensional parabolic mirror 123b and output to the detection unit 130.

The detection unit 130 includes: a non-polarizing beam splitter 131, a polarizing beam splitter 132, a detection element 133, an amplifier 134, a wave plate 135 and a control element 125. Through the optical property detected by the detection unit 130, the signal is sent to the process unit 140 for further analysis.

Users, through the adjustments of motorized stage 121 and the two-dimensional parabolic mirror 123a and 123b, can detect the object to maintain the incidence angle of laser at the largest angle that causes the largest change in refraction index in amplitude, or the best resonance angle for energy coupling to detect the changes caused by the refractive index of the medium.

However, hemisphere lens and the two-dimensional mirror will both cause the complexity in light path adjustment and beam path deflection after long time operation. Slight deflection in the light path of the incident light will cause an error in the incidence angle and the enlargement of deflection in the light path. This shortage will cause difficulty in the detection of the optical phase and the resonance angle for the receiving terminal, which might cause a detection error or, in the worst scenario, a situation of not being able to implement the detection. Moreover, the system needs to be used with two two-dimensional off-axis parabolic mirror 123a and 123b at the same time; This will cause much more difficulty in the adjustment of positions of the three optical components. Therefore, users cannot easily scan the full incident angle without changing the light path to the detection unit 130. When the implementation of the angle scanning with a large range without the occurrence of light path deflection is desired, it will take a long time to adjust the relative positions of the coupling prism and two off-axis parabolic mirrors as well as the path incident light. Moreover, due to the focusing effect of the hemisphere lens 124 and the two-dimensional parabolic mirror 123a and 123b, the activation spot of the incident light will be very small which can only be used for the detection of single spot or single channel. Moreover, this design is not equipped with a mirror that directs horizontal propagation light into vertical propagation, so it's not easy to be integrated into a microscopy system.

SUMMARY OF THE INVENTION

The invention provides an optical detection system which includes a light source unit, a control unit and a detection unit.

The light source unit provides a light source. The control unit includes a first mirror, a first one-dimensional off-axis parabolic mirror, a second one-dimensional off-axis parabolic mirror, a cylindrical lens and a second mirror.

The first mirror is used to receive light and the cylindrical lens is disposed between the first one-dimensional off-axis parabolic mirror and the second one-dimensional off-axis parabolic mirror, in which the first mirror directs the light into the first one-dimensional off-axis parabolic mirror. The first one-dimensional off-axis parabolic mirror directs the light into the cylindrical lens and the cylindrical lens directs the light into the second one-dimensional off-axis parabolic mirror. After that, the second one-dimensional off-axis parabolic mirror directs the light into the second mirror. The second mirror then output the light.

The detection unit is to detect the light coming from the control unit to output a signal.

Preferably, the control unit of which further includes a triangle mirror which includes a first reflection side and a second reflection side, wherein the first reflection side receives the light from the light source and direct the light into the first mirror. The second reflection side receives the light from the second mirror and directs the light to the detection unit.

Preferably, the control unit of which further includes a first stage motion controller and a second stage motion controller. The first stage motion controller is connected to the triangle mirror, and the second stage motion controller is connected to the first mirror and the second mirror.

Preferably, the described optical detection system further includes a process unit used to receive the signals for analysis afterwards.

Users control the incident angle of the light entering the cylindrical lens through the first stage motion controller, and implement multiple spots scanning with fixed incident light through the second stage motion controller, so as to detect the object and maintain the incidence angle of the light into the cylindrical lens at the largest angle that causes the largest change in amplitude or the best resonance angle for energy coupling to detect the changes caused by the refractive index of the medium.

The fixation of the light source unit and the detection unit of the present invention, accompanied with the properties that the incidence angle of the light can be adjusted and scanned, make it possible to implement surface plasmon wave measuring modes, such as resonance angle, amplitude, wavelength, phase, etc at the same time. The present invention has both the properties of a large dynamic range and high sensitivity; moreover, it is easy to adjust the light path. Also, the present invention can be easily integrated into a microscopy system, which makes the invention very practical.

The advantages and spirit of the present invention, and further embodiments can be further understood with the following embodiments and appended figures.

DETAILED DESCRIPTION OF THE INVENTION

For clarity of disclosure, and not by way of limitation, the detailed description of the invention is divided into the subsections that follow.

To further illustrate the present invention, the following specific examples are provided.

Figure 1:
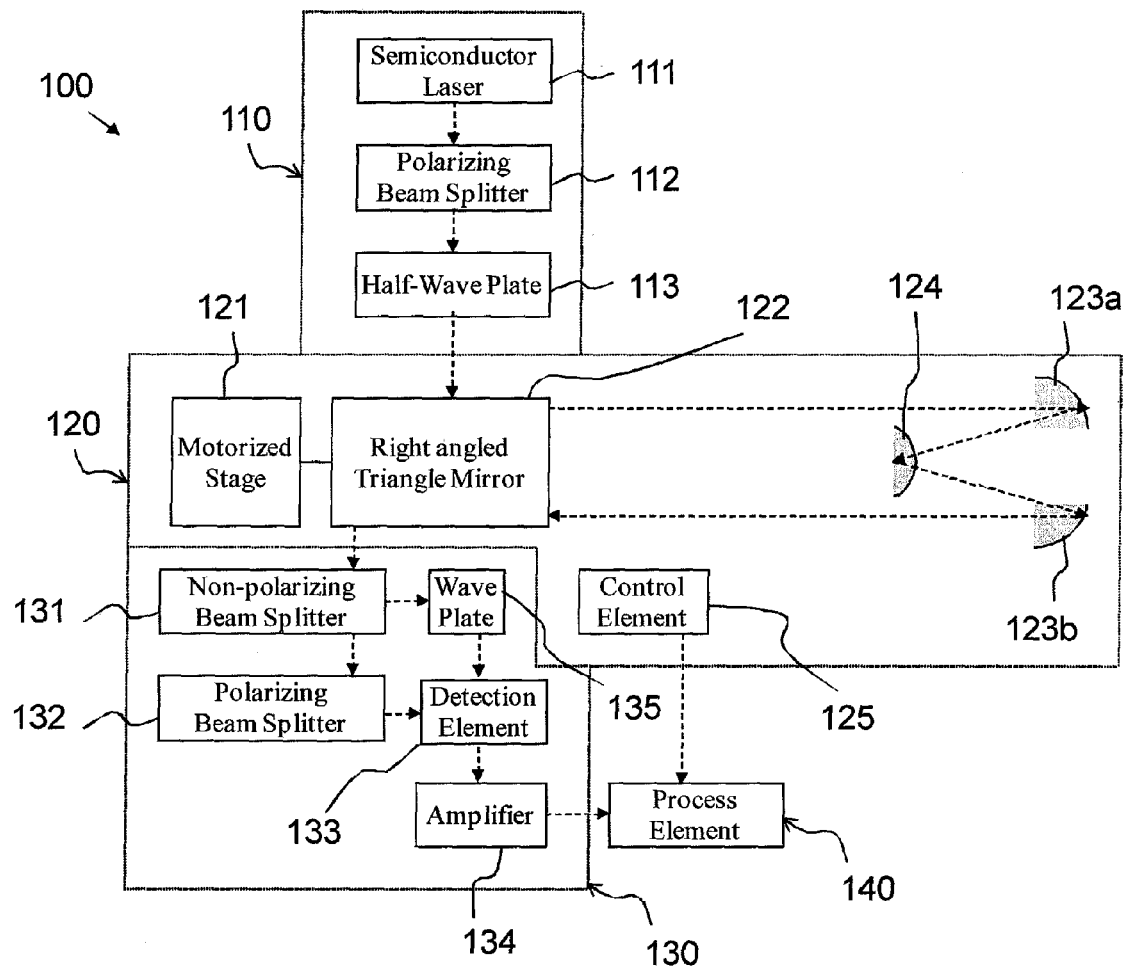
FIG. 1 illustrates the surface Plasmon wave detection system of prior art.
Figure 2:
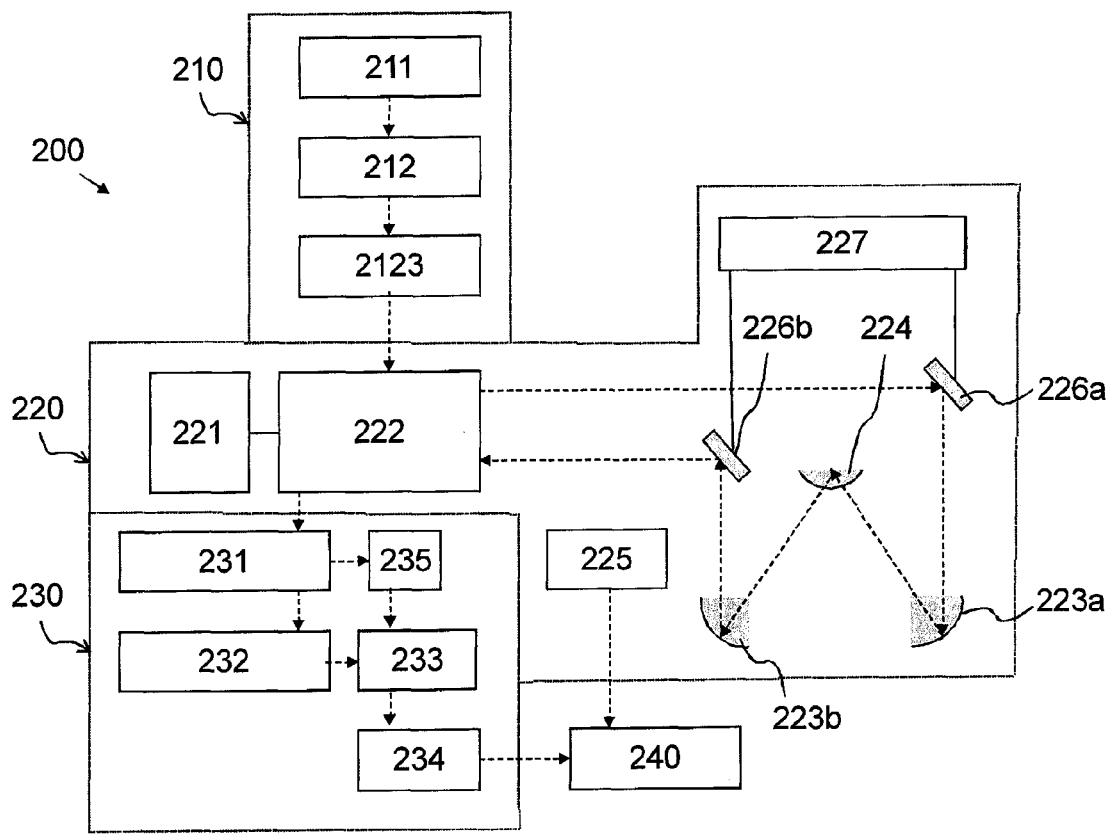
FIG. 2 illustrates the optical detection system.
Figure 3:
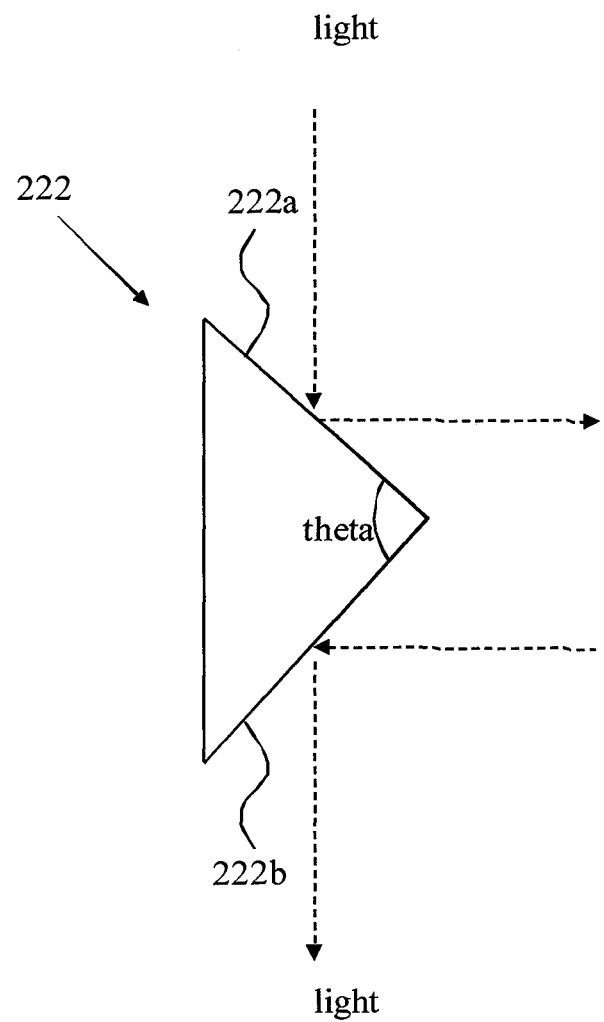
FIG. 3 illustrates the triangle mirror of the optical detection system.

FIG. 2 illustrates the optical detection system of the present invention and FIG. 3 illustrates the triangle mirror of the optical detection system of the present invention. In this embodiment, the optical detection system 200 of the present invention includes a light source unit 210, a control unit 220, a detection unit 230 and a process unit 240.

The light source unit 210 contains a semiconductor laser 211, a polarizing beam splitter 212 and a half-wave plate 213

The semiconductor laser 211 is to provide a light source, and the light is directed into the control unit 220 through polarizing beam splitter 212 and the half-wave plate 213. The semiconductor laser 211 can also be replaced by an LED or other light source, such as LED, not limited with the illustrated invention.

The control unit 220 includes a first stage motion controller 221, a triangle mirror 222, a first mirror 226a, a first one-dimensional off-axis parabolic mirror 223a, a second one-dimensional parabolic mirror 223b, a cylindrical lens 224, a control element 225, a second mirror 226b and a second stage motion controller 227, wherein the triangle mirror 222 has a first reflection side 222a and a second reflection side 222b. The incident planes of the first one-dimensional off-axis parabolic mirror 223a and the second one-dimensional off-axis parabolic mirror 223b are perpendicular to those of the first mirror 226a and the second mirror 226b, respectively. The cylindrical lens 224 is disposed symmetrically on the light axis between the first one-dimensional parabolic mirror 223a and the second one-dimensional parabolic mirror 223b.

After the light enters the control unit 220, the horizontal propagation light is directed into the first mirror 226a through the first reflection side 222a of the triangle mirror 222. The first mirror 226a converts the horizontal propagation light into vertical propagation light toward the first one-dimensional off-axis parabolic mirror 223a. After that, the first one-dimensional off-axis parabolic mirror 223a directs the light into the cylindrical lens 224 and evanescent waves are generated on the part of the plane through reflection. After that, the cylindrical lens 224 directs the light to the second one-dimensional parabolic mirror 223b. Likewise, the second one-dimensional off-axis parabolic mirror 223b converts the light into vertical propagation light toward the second mirror 226b. At last, the vertical propagation light is converted back to horizontal propagation light by the second mirror 226b, and directed back to the second reflection side 222b of the triangle mirror 222 to be output by the second reflection side 222b of the triangle mirror 222 to the detection unit 230, wherein the output light of the second mirror 226b is parallel with the incident light of the first mirror 226a.

In the embodiment above, the angle (denoted as theta) of the two mirrors of the triangle mirror 222 is not limited to a right angle (90 degrees), and the equation of the displacement of the mirror ($L_M$) and that of incident light beam ($L_B$) is $L_B=L_M*\sin(theta)$. When the theta between the two reflection sides of the triangle mirror 222 is not 90 degrees, sin(theta) is the enhancing factor of light displacement resolution. When the theta is 90 degrees, the light reflected by the second reflection side 222b will coincide with the incident light of the first reflection side 222a.

In one embodiment, the triangle mirror 222 can be replaced by a mirror or a polarizing or non-polarizing beam splitter, which is not limited with the illustrated invention. In one embodiment, the triangle mirror 222 can be a mirror, not limited with the illustrated invention.

In one embodiment, the first mirror 226a and the second mirror 226b can be a singular mirror, not limited with the illustrated invention.

In one embodiment, the first one-dimensional off-axis parabolic mirror 223a and the second one-dimensional off-axis parabolic mirror 223b can be one non-separate parabolic mirror or two one-dimensional parabolic mirrors with different specifications, not limited with the illustrated invention.

In one embodiment, the central angle between the first one-dimensional off-axis parabolic mirror 223a and the second one-dimensional off-axis parabolic mirror 223b is 40°~50°, the focal length is 45~55 mm, the diameter is 1~3 inches, wherein 45° is the best central angle, 50.8 mm is the best focal length, and 2 inches is the best diameter, not limited with the illustrated invention.

In one embodiment, the cylindrical lens 224 can be a semi-cylindrical lens, disposed on a symmetrical axis between the first one-dimensional off-axis parabolic mirror 223a and the second one-dimensional off-axis parabolic mirror 223b, not limited with the illustrated invention.

In one embodiment, the first stage motion controller 221 is connected to a motorized translation stage (not illustrated) where the triangle mirror 222 is located to provide the power and signal needed for moving the reflection position of the light on the triangle mirror 222. By the movement of the motorized translation stage, the incidence angle of the light that goes in the cylindrical lens 224 can be changed.

Figure 4:
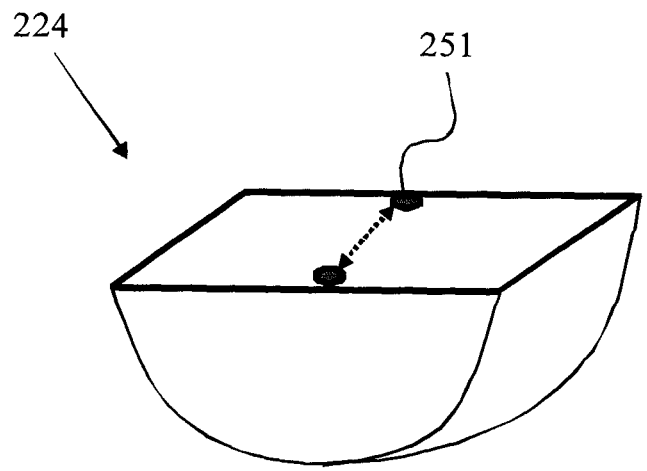
FIG. 4 illustrates the application of the optical detection system of the present invention to multiple spots detection.

In one embodiment, the second stage motion controller 227 is connected to another motorized translation stage (not illustrated) where the first mirror 226a and the second mirror 226b (the first mirror 226a and the second mirror 226b can be one mirror) are located, which provides the power and signal needed for moving the reflection position of the light on the first mirror 226a and the second mirror 226b. By the movement of the motorized translation stage, the light can be guided to implement linear scanning with fixed incidence angle on the plane part of the cylindrical lens 224. Moreover, in this embodiment, as illustrated in FIG. 4, the light source provided by light source unit 210 is a spot, and the light 251 is generated by the spot light source on the plane of the cylindrical lens 224; therefore, when the optical detection system 200 of the present invention is applied to surface Plasmon wave biomedical detection element, multiple spots detection can be implemented.

Figure 5:
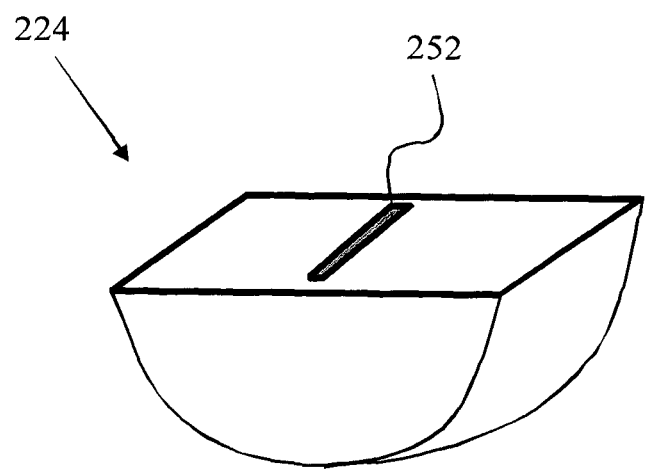
FIG. 5 illustrates the application of the optical detection system of the present invention to simultaneous detection of multiple spots with multiple channels or linear distribution.

In another embodiment, as illustrated in FIG. 5, if the light provided by the light source unit 210 is a linear light source, the light 252 is generated by the linear light source on the plane of the cylindrical lens 224, and the optical detection system 200 of the present invention can implement multiple channels or linear multiple spots simultaneous detection. The second stage motion controller 227 can then be removed, which is not limited with the illustrated invention.

The control unit 225 is electrically connected to the first stage motion controller 221 and/or the second stage motion controller 227 to control the movement and the position of the motorized translation stages.

The detection unit 230 includes a Non-polarizing beam splitter 231, a polarizing beam splitter 232, at least a detection element 233, an amplifier 234 and a wave plate 235. The detection unit 230 detects the light property and generates a signal, and then transmits the signal to the process unit 240 for further analysis. In one embodiment, the detection element 233 can be a photodiode, a CCD image sensor or a CMOS image sensor and the wave plate 235 can be ¼ wave plate, not limited with the illustrated invention.

The process unit 240 is used to receive the signals for further analysis. Meanwhile, the control element 225 of the control unit 220 is also electrically connected to the process unit 240. With the process unit 240, signals can be transmitted to control the control element 225. Therefore, the process unit 240 can process the signals received from the detection unit 230 and the control unit 220. In one embodiment, the process unit 240 can be a computer, not limited to the illustrated invention.

Users can detect the object and make the incidence angle of the light that goes in the cylindrical lens 224 fixed at the angle that causes the largest change in amplitude, or the best resonance angle for energy coupling to detect the changes caused by the refractive index of the medium using the first stage motion controller 221, the second stage motion controller 227, the first one-dimensional off-axis parabolic mirror 223a, and the second one-dimensional off-axis parabolic mirror 223b, accompanied with the adjustment of the first mirror 226a and the second mirror 226b. Due to the one-dimensional mode of the parabolic mirror, the light path is simple. As a result, the adjustment of the incidence angle of light can be achieved under the circumstance that both the light source unit and the detection unit are fixed (i.e. the positions of transmitting and receiving light are fixed). Moreover, the light path is easy to adjust, so it's very practical.

The embodiments above are only used to illustrate the principles and effects of the present invention but not limit the invention. Therefore, a skilled person in the art can modify or change the embodiments mentioned above without departing from the spirit of the present invention. The scope of the present invention is defined by the appended claims listed below.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. An optical detection system, including:
   a light source unit, used to provide light;
   a control unit, including:
   a first mirror, used to receive light;
   a first one-dimensional off-axis parabolic mirror;
   a second one-dimensional off-axis parabolic mirror;
   a cylindrical lens, disposed between the first one-dimensional off-axis parabolic mirror and the second one-dimensional off-axis parabolic mirror;
   a second mirror; and
   a triangle mirror, having a first reflection side and a second reflection side; and
   a detection unit;
   wherein, the first reflection side of the triangle mirror receives light from the light source unit and directs the light into the first mirror, the first mirror directs the light into the first one-dimensional off-axis parabolic mirror, and the first one-dimensional off-axis parabolic mirror directs the light into a cylindrical lens, and the cylindrical lens directs the light to the second one-dimensional off-axis parabolic mirror; the second one-dimensional off-axis parabolic mirror directs the light to the second mirror; the second mirror then output the light; the second reflection side of the triangle mirror receives light from the second mirror and directs the light into the detection unit, and the detection unit detects the light coming from the control unit to output a signal.

2. The optical detection system according to claim 1, wherein the light source unit includes a semiconductor laser or an LED light source.

3. The optical detection system according to claim 1, wherein the light source unit further includes a polarizing beam splitter and a half-wave plate.

4. The optical detection system according to claim 1, wherein the control unit further includes a first stage motion controller connected to the triangle mirror.

5. The optical detection system according to claim 4, wherein the triangle mirror is located at a motorized translation stage.

6. The optical detection system according to claim 4, wherein the control unit further includes a second stage motion controller connected to the first mirror and the second mirror.

7. The optical detection system according to claim 6, wherein the first minor and the second minor are located at a motorized translation stage.

8. The optical detection system according to claim 6, wherein the control unit further includes a control element electrically connected to the first stage motion controller and/or the second stage motion controller.

9. The optical detection system according to claim 1, wherein the incident planes of the first one-dimensional off-axis parabolic minor and the second one-dimensional off-axis parabolic mirror are perpendicular to the incident planes of the first minor and the second minor, respectively.

10. The optical detection system according to claim 1, wherein the first minor and the second minor are a single minor.

11. The optical detection system according to claim 1, wherein the first one-dimensional off-axis parabolic minor and the second one-dimensional off-axis parabolic minor are either two one-dimensional off-axis parabolic minors with different specifications or one single parabolic minor.

12. The optical detection system according to claim 1, wherein the cylindrical lens is a semi-cylindrical lens.

13. The optical detection system according to claim 1, wherein the cylindrical lens is disposed on the symmetric axis between the first one-dimensional off-axis parabolic mirror and the second one-dimensional off-axis parabolic mirror.

14. The optical detection system according to claim 1, wherein the detection unit includes a non-polarizing beam splitter, a polarizing beam splitter, an amplifier, a wave plate and at least a detection element.

15. The optical detection system according to claim 14, wherein the detection element is a photodiode, a CCD image sensor or a CMOS image sensor.

16. The optical detection system according to claim 1, wherein further includes a process unit.

17. The optical detection system according to claim 16, wherein the process unit is a computer.

18. The optical detection system according to claim 1, wherein the triangle mirror is a polarizing or non-polarizing beam splitter.

* * * * *